(12) United States Patent
Vaidya et al.

(10) Patent No.: US 8,224,583 B2
(45) Date of Patent: Jul. 17, 2012

(54) SYSTEM AND METHOD FOR PROVIDING OPTIMAL CONCENTRATIONS FOR MEDICATION INFUSIONS

(75) Inventors: Vinay Vaidya, Scottsdale, AZ (US); Elora Hilmas, Baltimore, MD (US); LeAnthony Matthews, Ridgeland, MS (US); Mohamed Gaffoor, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/873,016

(22) Filed: Aug. 31, 2010

(65) Prior Publication Data

US 2011/0004189 A1    Jan. 6, 2011

Related U.S. Application Data

(62) Division of application No. 11/065,026, filed on Feb. 25, 2005, now Pat. No. 7,813,880.

(60) Provisional application No. 60/556,075, filed on Mar. 25, 2004, provisional application No. 60/632,093, filed on Dec. 1, 2004.

(51) Int. Cl.
*G01N 33/48* (2006.01)
*G06F 17/00* (2006.01)
*G06Q 10/00* (2012.01)

(52) U.S. Cl. ................ 702/19; 700/90; 702/20; 703/11; 705/2

(58) Field of Classification Search ........................ None
See application file for complete search history.

*Primary Examiner* — Shubo Zhou
(74) *Attorney, Agent, or Firm* — Evans & Molinelli PLLC; Eugene J. Molinelli (57) ABSTRACT

Techniques for medical infusions include determining a first infusion rate for administering a first medication to a patient. A fluid load is determined based at least in part on the first infusion rate. It is determined whether the fluid load exceeds a predetermined threshold based on a fluid maintenance rate. If it is determined that the fluid load exceeds the predetermined threshold, then an action is caused to inhibit administering the first medication to the patient at the first infusion rate.

17 Claims, 8 Drawing Sheets

(2) DOPAMINE* CONCENTRATIONS

| | CONCENTRATIONS | FLUID LOAD | | | LEAST INCREMENT | |
|---|---|---|---|---|---|---|
| | | ml/hr | ml/kg/d | % MAINT. | 0.1 ml/hr = 1DOSE | |
| ⦿ 2) | PREMIX #1 800 mCg/ml | | | | 2.00 | mcg/kg/min |
| ○ 3) | PREMIXED #3 3200 mCg/ml | 0.1 | 4.8 | 4% | | mcg/kg/min |
| ○ 4) | MAXIMUM 6400 mCg/ml | 0.02 | 1 | 1% | | mcg/kg/min |
| ○ 5) | CUSTOM _____ mCg/ml | 0.01 | 0.5 | | | mcg/kg/min |
| ○ 6) | RULE OF 60 (X 10) 300 mCg/ml | 0.2 | 10 | 8% | 1.00 | mcg/kg/min |

TEST PATIENT WEIGHT (kg)  0.5 ▲▼
TEST DOSE (mcg/kg/min)    0.5 ▲▼

DRIP VOLUME WITHIN 8% OF MAINTENENCE FLUIDS

OK

SHOW TABLE

| DWI TABLE | | 2 | 3 | 4 | 5 | 6 | DOPAMINE* DRIP 7 | 8 | 9 | 10 | LOW CONC. (=600 mCg/ml) 11 | 12 | 13 | RATE in ml 19 | 25 |
|---|---|---|---|---|---|---|---|---|---|---|---|---|---|---|---|
| DOSE: mcg/kg/min | | | | | | | | | | | | | | | |
| FLUID ml/kg/da | → | 5 | 7 | 10 | 12 | 14 | 17 | 19 | 22 | 24 | 26 | 29 | 31 | 46 | 60 |
| | WEIGHT | | | | | | | | | | | | | | |
| NICU | 0.5 kg | 0.1 | 0.2 | 0.2 | 0.3 | 0.3 | 0.4 | 0.4 | 0.5 | 0.5 | 0.6 | 0.6 | 0.7 | | |
| | 1.5 kg | 0.2 | 0.3 | 0.4 | 0.5 | 0.6 | 0.7 | 0.8 | 0.9 | 1 | 1.1 | 1.2 | 1.3 | 1.9 | |
| | 2.0 kg | 0.4 | 0.6 | 0.8 | 1 | 1.2 | 1.4 | 1.6 | 1.8 | 2 | 2.2 | 2.4 | 2.6 | 3.8 | |
| | 3.0 kg | 0.6 | 0.9 | 1.2 | 1.5 | 1.8 | 2.1 | 2.4 | 2.7 | 3 | 3.3 | 3.6 | 3.9 | 5.7 | |
| | 4.0 kg | 0.8 | 1.2 | 1.6 | 2 | 2.4 | 2.8 | 3.2 | 3.6 | 4 | 4.4 | 4.8 | 5.2 | | |
| PICU | 5.0 kg | 1 | 1.5 | 2 | 2.5 | 3 | 3.5 | 4 | 4.5 | 5 | 5.5 | 6 | 6.5 | | |
| | 7.5 kg | 1.5 | 2.3 | 3 | 3.8 | 4.5 | 5.3 | 6 | 6.8 | 7.5 | 8.3 | 9 | 9.8 | | |
| | 10.0 kg | 2 | 3 | 4 | 5 | 6 | 7 | 8 | 9 | 10 | 11 | 12 | 13 | | |
| | 15.0 kg | 3 | 4.5 | 6 | 7.5 | 9 | 10.5 | 12 | 13.5 | 15 | 16.5 | 18 | 19.5 | | |
| | 20.0 kg | 4 | 6 | 8 | 10 | 12 | 14 | 16 | 18 | 20 | 22 | 24 | 26 | | |
| | 25.0 kg | 5 | 7.5 | 10 | 12.5 | 15 | 17.5 | 20 | 22.5 | 25 | 27.5 | 30 | 32.5 | | 62.5 |
| | 30.0 kg | 6 | 9 | 12 | 15 | 18 | 21 | 24 | 27 | 30 | 33 | 36 | 39 | | 75 |
| | 35.0 kg | 7 | 10.5 | 14 | 17.5 | 21 | 24.5 | 28 | 31.5 | 35 | | | | | 87.5 |
| | 40.0 kg | 8 | 12 | 16 | 20 | 24 | 28 | 32 | 36 | 40 | | | | | 100 |
| | 45.0 kg | 9 | 13.5 | 18 | 22.5 | 27 | 31.5 | 36 | | | | | | | 112.5 |
| | 50.0 kg | 10 | 15 | 20 | 25 | 30 | 35 | | | | | | | | 125 |
| ADULT | 55.0 kg | 11 | 16.5 | 22 | 27.5 | 33 | 38.5 | | | | | | | 104.5 | 137.5 |
| | 60.0 kg | 12 | 18 | 24 | 30 | 36 | 42 | | | | | | | 114 | 150 |
| | 65.0 kg | 13 | 19.5 | 26 | 32.5 | | | | | | | | | 123.5 | 162.5 |
| | 70.0 kg | 14 | 21 | 28 | 35 | | | | | | | | | 163 | 175 |

☑ SHOW TABLE

☑ Colored formatting

602 — Order form header:

> UNIVERSITY OF MARYLAND MEDICAL SYSTEM
> DEPARTMENT OF PHARMACY SERVICES - PHYSICIAN'S ORDER SHEET
> 1. All medication orders, including treatments containing medications, room and/or service
> 2. Drugs covered by the automatic stop order policy should be ordered for a specific number of doses.
> 3. Please provide all the required information. WEIGHT 12 kg HEIGHT _____
> 4. Please indicate your physician ID Number. ALLERGY Doe, John: MR No: 12121212

IMPRINT ORDER SHEET WITH PATIENT ID PLATE BEFORE USING — 610

(A) DOPAmine Drip (1600 mcg/ml) | Monday, Nov 1, 2004, 11:08 AM

Order MUST BE RENEWED BY noon on Tuesday, Nov 2/2004
DOPAmine Starting Dose = 5 mcg/kg/min
Rate = 2.3 ml/hour, IV
Drip Concentration = 1600 mcg/ml

SPECIAL INSTRUCTIONS:

604 — (B) Pharmacy/Compounding Instructions

! Dispense premixed bag (1600 mcg/ml), OR compound as below
MNEMONIC: std1600dopa2     Total 400 mg/250 ml D5W
Please highlight in yellow, the concentration (1600 mcg/ml) on the label ☐ Drip checked by 2 Pharmacists (Name/Initial/Date) ______ / ______
(1) From a vial containing, DOPAmine 40 mg/ml, draw 10 ml in a syringe. This equals 400 mg of DOPAmine drug
(2) Add it to 240 ml of D5W, to make a total drip volume of 250 ml
(3) Label the drip: DOPAmine drip: (1600 mcg/ml) in D5W

DOPAmine Drip (1600 mcg/ml)

606 — (C) Nursing Instructions, at Start & each shift change

(1) Confirm patient identity: Doe, John/ Mr# 12121212/ 12kg
(2) Confirm drip contains DOPAmine, Conc = 1600 mcg/ml
(3) Enter/confirm the following parameters in the infusion pump:
[i] DOPAMine concentration = 1600 mcg/ml
[ii] Patient's Weight = 12 kg

| [iii] Starting Dose = 5 mcg/kg/min | For all subsequent dose |
| [iv] Confirm pump rate = 2.3 ml/hour | changes see table (D) below |

(4) To double check the pump rate, either use the 'DOSING CHART'(E) on the right OR use the formula below in your calculator $$\text{Infusion rate} = \frac{\text{Dose} \times 12\,(\text{Weight}) \times 60\,(\text{minutes})}{1600\,(\text{Drip Conc.})}$$

Valid Nov-01 to noon on Nov-02

608 — (D) Dose change orders (Physicians to hand-enter orders)

| Date and Time | Dose | MD Initials | Nurse Initials |
|---|---|---|---|
| 11/01/04, 11:08:41 AM | 5 mcg/kg/min (Starting Dose) | | |
| | | | |
| | | | |
| | | | |
| | | | |

DOPAmine (1600 mcg/ml)

(E) DOSING CHART FOR 12 KG

| DOPAmine Dose | Infusion rate* |
|---|---|
| 2 mcg/kg/min | 0.9 ml/hour |
| 3 mcg/kg/min | 1.4 ml/hour |
| 4 mcg/kg/min | 1.8 ml/hour |
| 5 mcg/kg/min | 2.3 ml/hour |
| 6 mcg/kg/min | 2.7 ml/hour |
| 7 mcg/kg/min | 3.2 ml/hour |
| 8 mcg/kg/min | 3.6 ml/hour |
| 9 mcg/kg/min | 4.1 ml/hour |
| 10 mcg/kg/min | 4.5 ml/hour |
| 11 mcg/kg/min | 4.5 ml/hour |
| 12 mcg/kg/min | 5.4 ml/hour |
| 13 mcg/kg/min | 5.9 ml/hour |
| 14 mcg/kg/min | 6.3 ml/hour |
| 15 mcg/kg/min | 6.8 ml/hour |
| 16 mcg/kg/min | 7.2 ml/hour |
| 17 mcg/kg/min | 7.7 ml/hour |
| 18 mcg/kg/min | 8.1 ml/hour |
| 19 mcg/kg/min | 9 ml/hour |
| 21 mcg/kg/min | 9.5 ml/hour |
| 22 mcg/kg/min | 9.9 ml/hour |
| 23 mcg/kg/min | 10.4 ml/hour |
| 24 mcg/kg/min | 10.8 ml/hour |
| 25 mcg/kg/min | 11.3 ml/hour |

*Infusion rates rounded to 1 decimal place

Note: 1 mcg/kg/min = 0.45 ml/hour
Order MUST BE RENEWED by noon on Tue, Nov 2, 2004
Signature: ___ ___ ___ ___ ___ ___ ___ ___ ___
Ordered by:          Dr. Doctor
Page Number:         1234567
☐ Faxed to Pharmacy (B-7163)

! ALERT ! This dosing chart is applicable only for patient weighing 12 kg, and drip conc of 1600 mcg/ml

FIG. 7

| STEP 1 Enter patient data (all req'd fields) | |
|---|---|
| (a) Patient's Name | Doe, John |
| (b) Weight (kg) | 12 |
| (c) Medical record # | 12121212 |
| (d) Ordering physician | Dr. Doctor |
| (e) Physician Pager/Tel # | 1234567 |
| (g) Total fluid limit per day | 1 ▽△ times maintenance ▽  (=92 ml/kg/day 1,104 ml/day) |

HELP MESSAGES

Click to Select Help Topics ▽

CAUTION ! FENTANYL is a narcotic agent (respiratory depressant) and its use as a drip generally requires patients to be on MECHANICAL VENTILATION ! Consult attending physician if patient is not on mechanical ventilation !

| STEP 2 Select Drug/Dose | | | | STEP 2a: Optional | | | STEP 2b: Fluid Load (for info only) | |
|---|---|---|---|---|---|---|---|---|
| Star ? | Select Drug | Select Dose | Reference Dose Range | Drip conc (per ml) | Change Drip concentration | Enter Comment | Hourly Drip Rate (ml/hr) | Fluid Load (as % total fluid limit) |
| #1 | Fentanyl | ▽ | 1 to 10 mcg/kg/HOUR | | Change Conc | | | |
| #2 | Click to Select | ▽ | | | Change Conc | | | |
| #3 | Click to Select | ▽ | | | Change Conc | | | |
| #4 | Click to Select | ▽ | | | Change Conc | | | |
| #5 | Click to Select | ▽ | | | Change Conc | | | |

SUMMARY: The total hourly infusion rate from 1 drip(s) is. This equals 0% of total fluid limit per day, leaving the remainder 100 of fluids available for nutrition and other fluid needs.

| STEP 3 | Print Drip Order | Clear All Entries | Clear All Drips | Sample Patient |
|---|---|---|---|---|

Valid until    November 20, 2005    1 decimal place (infusion rate)

FIG. 8

SYSTEM AND METHOD FOR PROVIDING OPTIMAL CONCENTRATIONS FOR MEDICATION INFUSIONS

This application claims benefit as a Divisional of application Ser. No. 11/065,026, filed Feb. 25, 2005 the entire contents of which are hereby incorporated by reference as if fully set forth herein, under 35 U.S.C. §120. The parent application Ser. No. 11/065,026 claims the benefit of U.S. Provisional Application Nos. 60/556,075, filed on Mar. 25, 2004, and 60/632,093, filed on Dec. 1, 2004, all of which are hereby incorporated by reference in their entirety.

BACKGROUND

Field of the Invention

The present invention relates generally to providing optimal concentrations for drugs to be administered as medical infusions. More particularly, the present invention relates to providing two to four optimal concentrations for drugs administered as continuous infusions for compliance with JCAHO standards. Background of the Invention A recent mandate by the Joint Commission on Accreditation of Hospitals ("JCAHO") requires all pediatric hospitals to alter the manner in which they administer continuous medication infusions to critically ill infants and children. The mandate requires that hospitals choose from among only a few standard concentrations for drugs administered as continuous infusions for all pediatric infusions. Prior to the JCAHO mandate, infusion concentrations were calculated on the basis of a patient's weight. Due to weight variations between patients, each patient likely was assigned a different concentration. As a result, the range of potential concentrations was essentially limitless. The JCAHO mandate forces hospitals to limit this once unlimited range to only a few standard concentrations.

A problem that arises from the JCAHO mandate is that pediatric hospitals are unsure how best to determine these three concentrations. In an attempt to overcome this problem, many hospital pharmacists and medical directors are posting questions on email lists to determine what other hospitals have done to identify the two to four optimum concentrations. Some of the hospitals have developed their own list of three concentrations. Such individually determined concentrations generally vary from hospital to hospital, thereby defeating the very purpose of standardization as mandated by the JCAHO. Conventional techniques for determining the two to four optimum concentrations for about 40 commonly used drugs are tedious, time consuming, trial-and-error approaches that typically require input from physicians, nurses and pharmacists.

BRIEF SUMMARY OF THE INVENTION

When ordering a continuous drug infusion for a pediatric patient, it is crucial to select optimum drug concentration based on patient weight and dose. The resulting infusion rate (mL/hr) should be such that it is neither too low, resulting in imprecise drug delivery, nor too high, resulting in fluid overload. Embodiments of the present invention ensure that the infusion rate will not fall below the lowest acceptable rate indicated by the user. Based on the lowest acceptable rate, successively higher concentrations for larger patients or patients who require higher doses are determined to ensure sufficient drug concentration while avoiding excessive fluid load. According to embodiments of the present invention, the resulting fluid load is always less than 8% of the daily fluid allowance. Thus, embodiments of the present invention perform a dual function of first identifying optimum drug concentration (for example, optimum 2 to 4 ideal concentrations) for each drug, and then recommending one of these concentrations for each specific patient and drug-dose combination.

Based upon several inputs regarding the type of drug used, the weight of the patient, and the infusion process, embodiments of the present invention provide the two to four optimum concentrations for a drug to be administered as a continuous infusion. Moreover, embodiments of the present invention display how these three concentrations will suit the entire range of patient sizes in pediatrics (from the smallest premature infant to a large adolescent) as well as across the entire useable dose range. The time to determine these concentrations according to embodiments of the present invention typically is less than one minute. Reviewing the results of the program and ascertaining that the concentrations selected by the program are appropriate typically requires another five minutes or so. Thus, embodiments of the present invention help determine concentrations for all 40 drugs within 3 to 4 hours. Conventional techniques, on the other hand, typically require weeks or even longer to determine these concentrations.

Beyond significantly reducing the time required for individual hospitals to determine optimal drug infusion concentrations, another advantage provided by embodiments of the present invention is that it enables multiple hospitals to act in a collaborative manner to determine the two to four optimum concentrations. Thus, instead of each hospital determining its own optimum standard concentrations. Such collaboration can lead to consensus, for example, on a national level thereby truly standardizing the process and enhancing patient safety.

Other benefits of the present invention include:
1. Assisting identification of the optimum concentration to the ordering physician from a choice of two to four possible concentrations. This identification takes into account patient weight and dose and, based on these parameters, suggests the best choice;
2. Providing a dose-weight-infusion rate chart that can be used by nurses to correctly infuse the medications thereby avoiding medication errors; and
3. Providing pharmacists with precise instructions on how to compound medications, thereby reducing chances of compounding errors.

BRIEF DESCRIPTION OF THE DRAWINGS

FIG. 6 is an exemplary order sheet according to embodiments of the present invention.

DETAILED DESCRIPTION OF THE INVENTION

Embodiments of the present invention assist medical practitioners in determining a plurality of optimum concentrations for drugs to be administered as continuous infusions in pediatric patients, such as critically ill infants and children. For example, in a preferred embodiment of the present invention, three optimum concentrations (low, intermediate and high) are provided. A drug to be administered as a medical infusion is predetermined for administration to the patient.

In one embodiment, the present invention is a computer program executing on a personal computer. Typically such computers include a microprocessor, internal memory, external mass storage (including, for example, disk or CD-ROM) and communication bus structure. In addition, such computers typically include an entry device such as a keyboard, a pointing device such as a mouse, output devices such as a display screen and a printer. Such personal computers are well-known in the art and need not be described further.

Using data input by a user, ideal concentrations that suit the needs of an entire range of pediatric patients are determined and displayed to the user. In a preferred embodiment of the present invention, this range extends from the smallest premature infant (approximately half a pound in weight) to a large adolescent patient (as much as 200 pounds in weight), and across all dose ranges (from minimum to maximum dose). In addition to determining the ideal drug concentrations, embodiments of the present invention allow users to select the optimal concentration tailored to the needs of the individual patient. In addition, this information may be displayed in a table with automatic programmed color-coding to enable users to visually identify the optimum concentration for a patient of a certain weight and/or requiring a certain dose range. Alternative concentration indicators such as gray scaling or cross hatching can be used.

Figure 1:
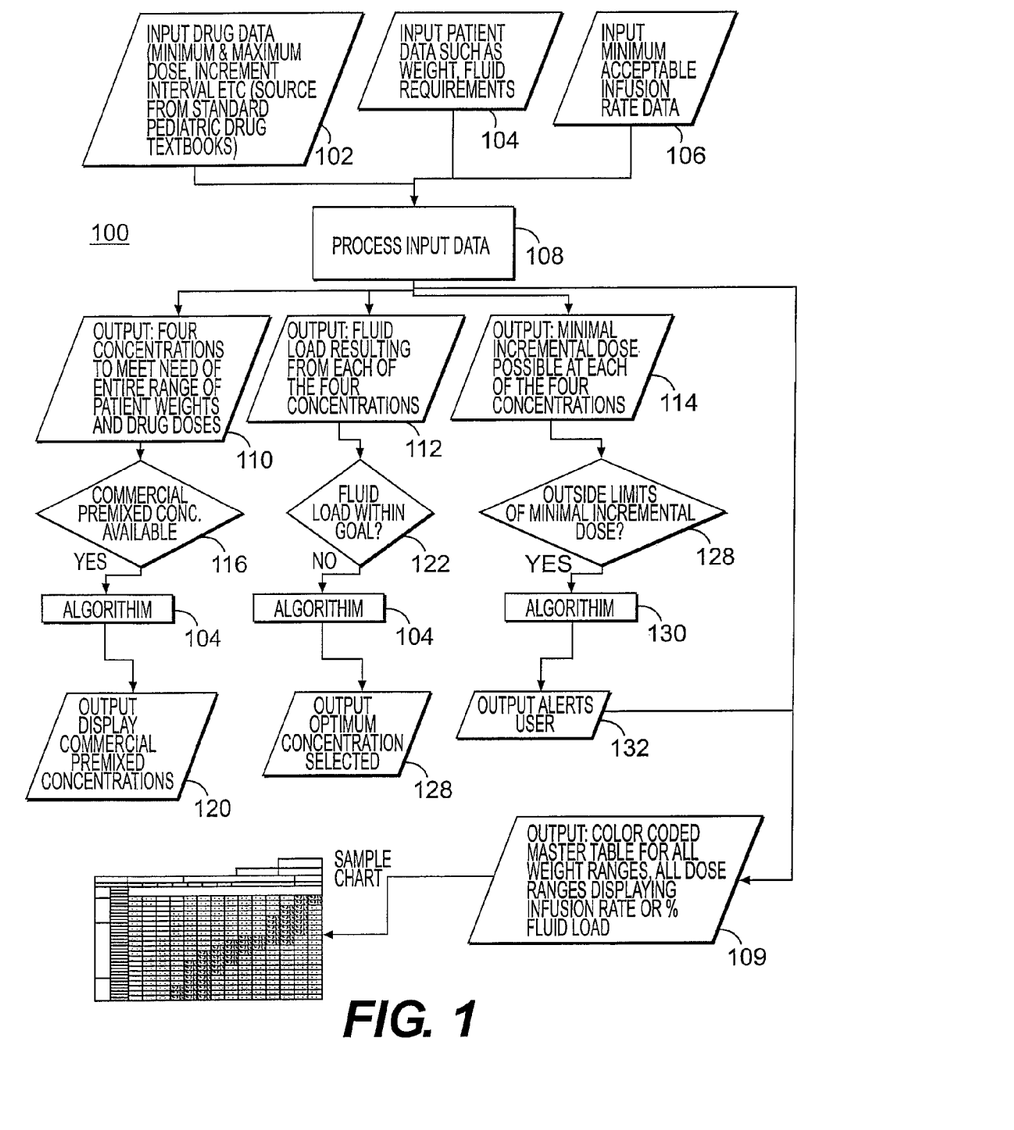
FIG. 1 is a flow chart for a method for providing optimal concentrations for drugs administered as medical infusions according to an embodiment of the present invention.

FIG. 1 is a flow chart 100 for a method for providing optimal concentrations for drugs administered as medical infusions according to an embodiment of the present invention. In steps 102, 104 and 106 input data is entered, for example, by a user. This input data includes data about the drug to be administered, the patient and the infusion process. The drug input data can typically be found in standard drug reference texts that are well-known to those skilled in the art. In an embodiment of the present invention, the drug input data is stored in a database accessible to the personal computer on which a computer program embodiment of the present invention executes. The database includes information describing each drug considered by an embodiment of the present invention. According to one embodiment of the present invention, the database includes the following information describing each drug:

(1) drug name;
(2) minimum dose;
(3) maximum dose;
(4) dose increment interval;
(5) dose units;
(6) low concentration;
(7) intermediate concentration;
(8) high concentration;
(9) maximum concentration;
(10) maximum peripheral and central concentrations permitted;
(11) commercially available premixed concentrations;
(12) commercially available premixed concentrations stocked locally;
(13) concentration of drug in vials;
(14) vial concentrations stocked daily;
(15) reference text source;
(16) rule of six concentration;
(17) rounding factor;
(18) multiplication factor;
(19) lowest patient weight in whom drug is used;
(20) lowest acceptable infusion rate;
(21) whether drug used as bolus;
(22) drug included in Pediatric Advanced Life Support Manual;
(23) drug stocked locally in cardiac arrest cart;
(24) drug used to treat arrhythmias;
(25) drug used in transport;
(26) concentration used in cardiac arrest situation;
(27) pharmacy mnemonic;
(28) volume of drug infusion used;
(29) volume of commercially available premixed drugs;
(30) diluent used for dip;
(31) generic name of drug;
(32) replace trade name with generic name;
(33) drug specific help information;
(34) therapeutic category;
(35) need for mechanical ventilation;
(36) drug dosage intervals;
(37) maximum drug amount to be dispensed at one time;
(38) adult dosing formula if applicable; and
(39) recommended concentration based on weight category.

Such drug input data includes minimum and maximum dose and increment interval. Patient data includes data such as the patient's weight and fluid requirements. Infusion data includes data about the infusion process such as the acceptable infusion rate.

Figure 2:
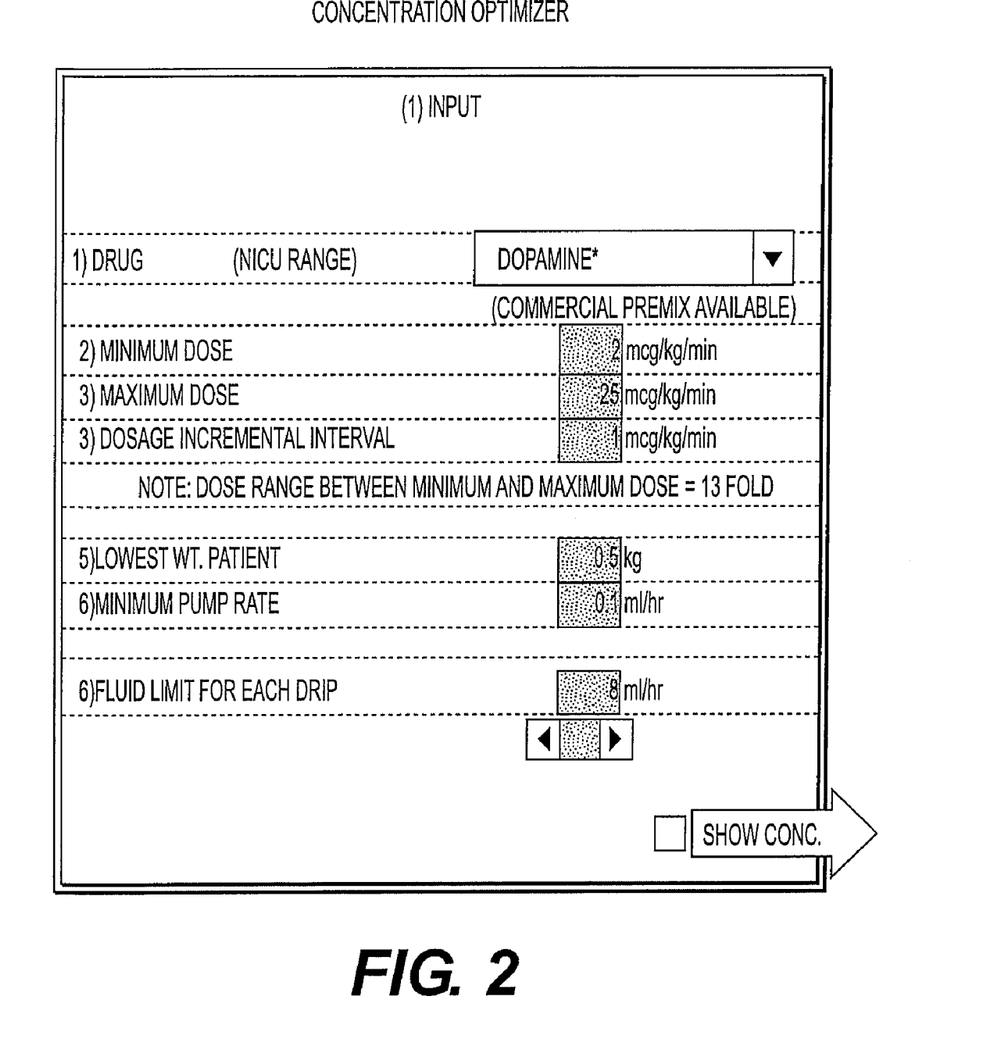
FIG. 2 is an exemplary format for obtaining input data according to an embodiment of the present invention.

FIG. 2 is an exemplary data input format for obtaining the required input data from a user. As shown in FIG. 2, inputs according to an exemplary embodiment of the present invention include:

(1) minimum dose;
(2) maximum dose;
(3) dose increment;
(4) lowest patient weight (in whom the medication will be used);
(5) lowest acceptable infusion rate (minimum pump rate); and
(6) total fluid intake goal (fluid limit).

In addition, two other inputs are used in the exemplary embodiment of the present invention. These are:

(7) maximum allowable fluid load resulting from infusion of one medication; and
(8) maximum permitted concentration for each medication.

In step 108, the input data is processed to determine the two to four optimum concentrations (low, intermediate, high and super high). In one embodiment of the present invention, the lowest concentration is the one that results in the lowest acceptable infusion rate at the lowest dose for the lowest weight patient and the highest concentration is predetermined based on published pharmacological data. In such an embodiment of the present invention, the intermediate concentration is then determined based on the range between the minimum and maximum dose. Moreover, embodiments of the present invention can default to commercially available premixed concentrations whenever such premixed concentrations are available.

For example, according to one computer-based embodiment of the present invention, the computer program processes the data as follows:

1. Low concentration is determined by the computer program as follows:
   a) First, the drug information sheet built into the program to see if only one concentration is permitted for a particular drug. The drug information sheet contains information related to various drugs. The information can be found in standard drug texts that are well-known to those skilled in the art. If the answer is yes, then the Final Low Concentration equal to the only permitted concentration is displayed.
   b) Next, the Preliminary Low Concentration using the following formula is calculated:

Preliminary low concentration=Lowest patient weight multiplied by Lowest dose divided by lowest pump infusion rate.

c) Next, the Preliminary Low Concentration is compared to the maximum permitted concentration. If the Preliminary Low Concentration is greater, the algorithm displays the Final Low Concentration value equal to half the value of the maximum concentration.
   d) The drug information sheet is then checked to see if there is a commercially available premixed concentration and if so, whether the available premixed concentration is less than the calculated Preliminary Low concentration. If it is less, then the Premix concentration is displayed as the Final Low concentration. If it is not less, then the Preliminary Low Concentration is displayed as the Final Low Concentration.
2. The Intermediate Concentration is determined by the computer program as follows:
   a) The ratio of maximum to the minimum dose range is calculated. If the calculated ratio is greater than 20, 4 times the value of the Low Concentration is displayed as the Intermediate Concentration. If the calculated ratio is less than 20, 2 times the value of the Low concentration is displayed as the Intermediate Concentration.
   b) Then, the Intermediate Concentration calculated in 2(a) is compared to the Maximum permitted concentration. If the Intermediate Concentration is greater, the value of Maximum Concentration divided by two is calculated. If the result of the calculation is greater than the Low Concentration calculated in 2(a), the result of the calculation is displayed as the Intermediate Concentration.
3. The High Concentration is determined by the program algorithm as follows
   a) If the ratio of maximum dose to minimum dose is greater than 20, then the High Concentration is calculated as four times the Intermediate Concentration. If the ratio is greater than 10 but less than 20, the High Concentration is calculated as three times the Low Concentration. If the ratio is less than 10, then the High Concentration is calculated as two times the intermediate concentration.

Figure 3:
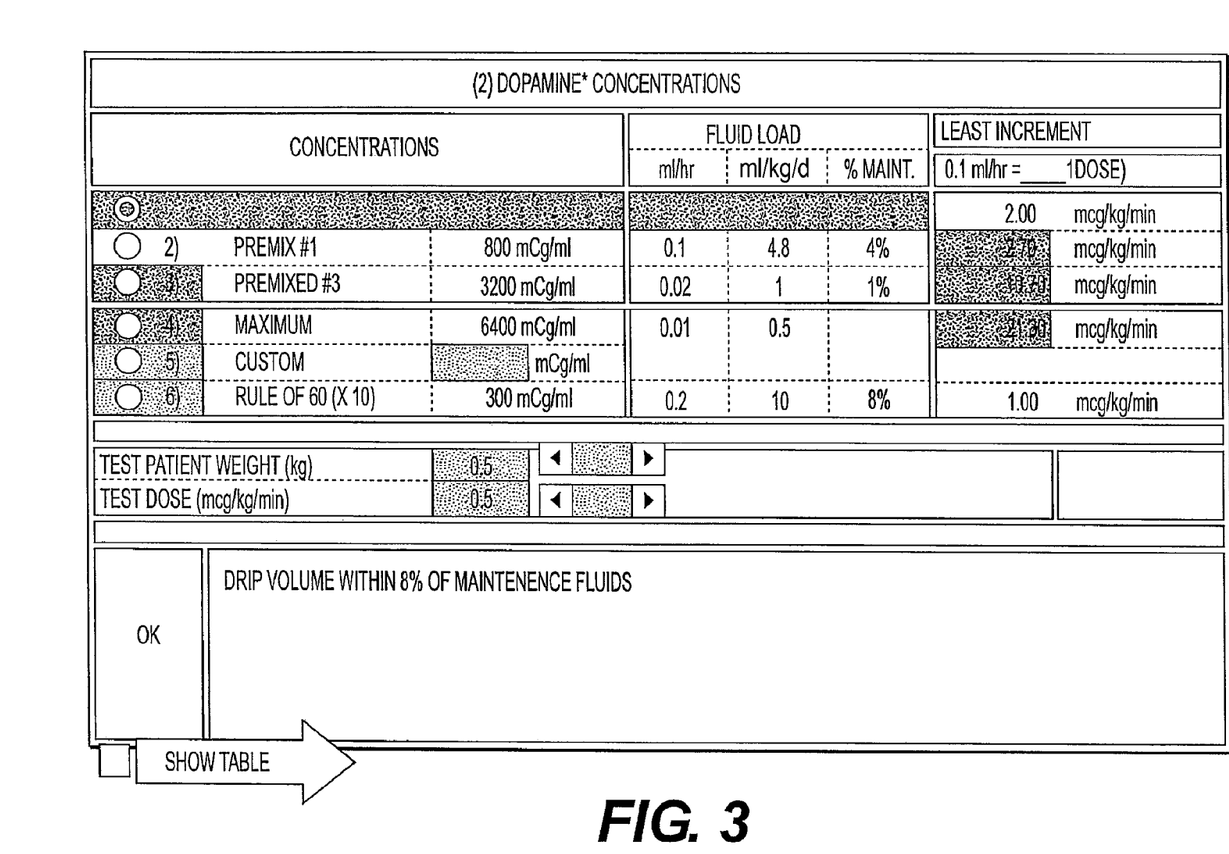
FIG. 3 is an exemplary output showing four determined concentrations and other information corresponding to the input illustrated in FIG. 2.

The outputs of processing step 108 are illustrated in steps 110, 112 and 114. The output illustrated by step 110 is the two to four concentrations. The output illustrated by step 112 is the fluid load resulting from each of the two to four concentrations. The output illustrated by step 114 is the minimal incremental does for each of the four concentrations. FIG. 3 is an exemplary output showing four determined concentrations and other information corresponding to the input illustrated in FIG. 2.

In step 116, the availability of commercially premixed concentrations of a particular drug is determined. This information can be stored, for example, in the drug information sheet described above. If such premix concentrations are available, then in step 118, it is determined whether the commercially available concentration falls close to one of the Low, Intermediate or High Concentration. If they do fall close, then in step 120, the one or more of these concentrations falling close is replaced with the closest commercially available premixed concentration In step 122, it is determined whether the fluid load is within a goal, i.e., within a desired clinical range. If the fluid load is not within the goal, then in step 124 the optimal concentration out of a choice of the 2 to 4 that were determined is selected in order to bring the fluid load within the desired clinical range. The selected concentration is then displayed in step 126.

In step 128, it is determined whether the minimal possible incremental dose is outside acceptable limits. In step 130, the amount of drug delivered at the lowest infusion rate of 0.1 milliliter per hour is calculated. If the amount of drug at this infusion rate is greater than two times the increment interval, the program alerts the user in step 132.

Figure 4:
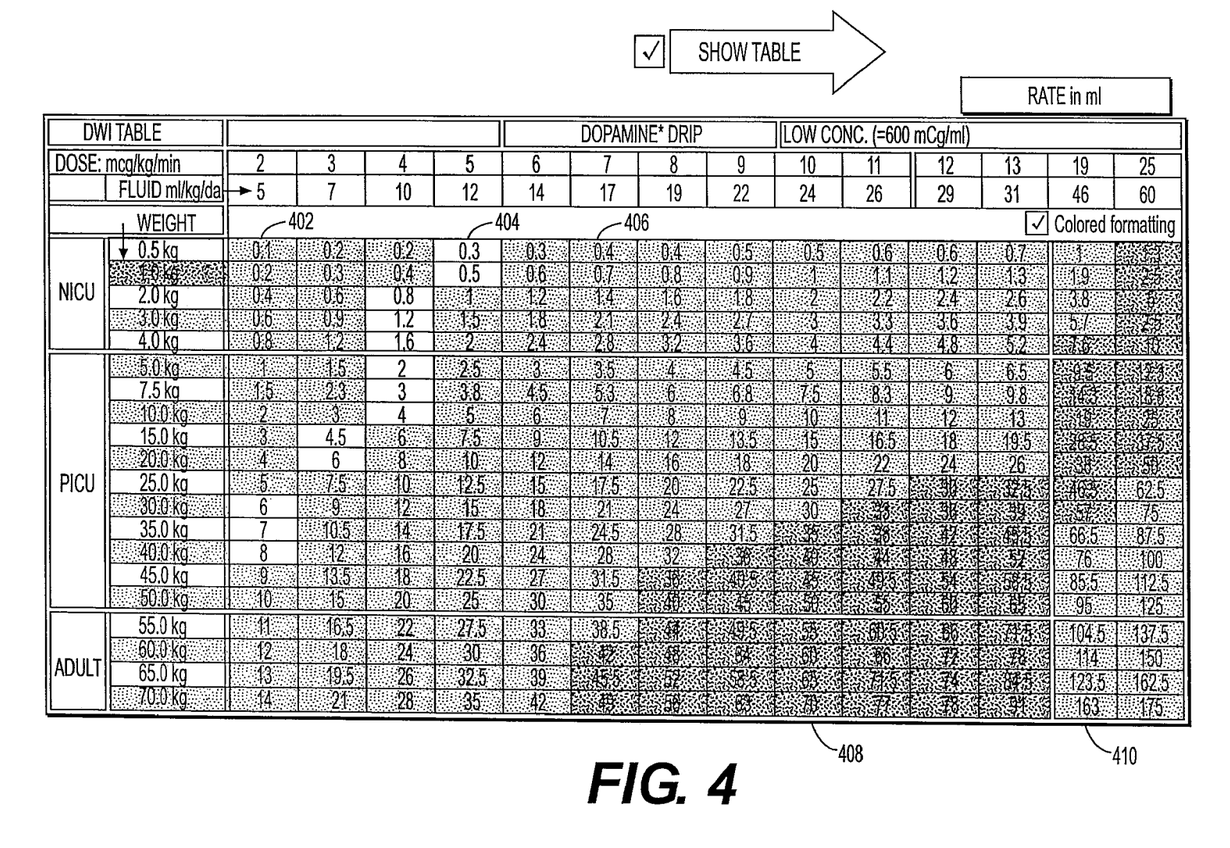
FIG. 4 is an exemplary table of calculated infusion rates at different doses output by an embodiment of the present invention.

In step 109, a table showing calculated infusion rates at different doses and different weights is displayed. In an embodiment of the present invention, the infusion rates are programmatically color-coded to identify the correct selection of concentration for any given weight and dose in order that the resulting fluid load is within the clinically desired range. In alternate embodiments of the present invention, the infusion rates are distinguished using gray scaling or cross hatching. FIG. 4 is an exemplary table of calculated infusion rates at different doses output by an embodiment of the present invention. Concentration boundaries are illustrated by sections 402 (low), 404 (intermediate), 406 (high), 408 (maximum) and 410 (exceeded maximum) respectively.

Figure 5:
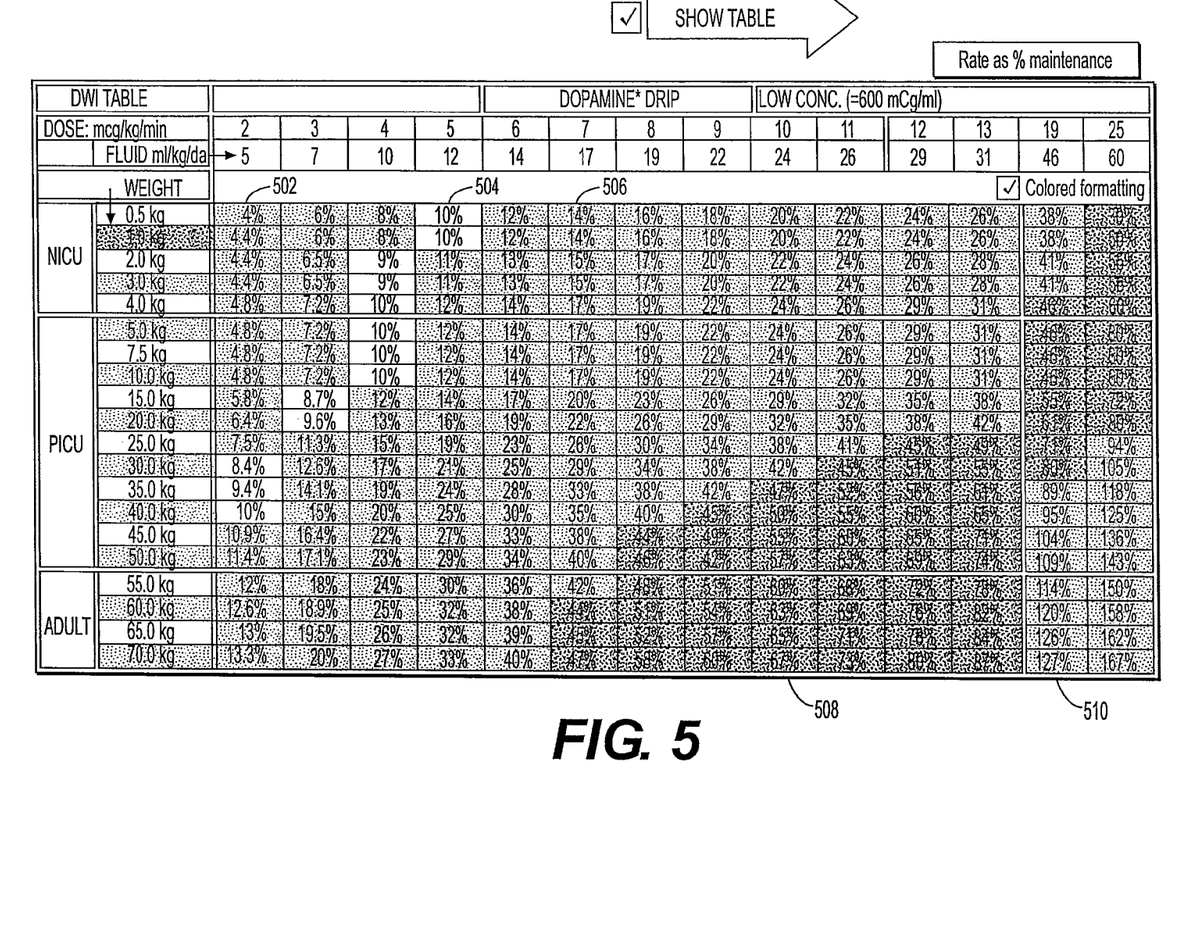
FIG. 5 is an exemplary table of percentage of maintenance corresponding to the infusion rate data shown in FIG. 4.

The table can also be output to show the percentage of maintenance corresponding to the calculated infusion rates at different doses. FIG. 5 is an exemplary table of percentage of maintenance corresponding to the infusion rate data shown in FIG. 4. In FIG. 5, concentration boundaries are illustrated by sections 502 (low), 504 (intermediate), 506 (high), 508 (maximum) and 510 (exceeded maximum) respectively.

Figure 7:
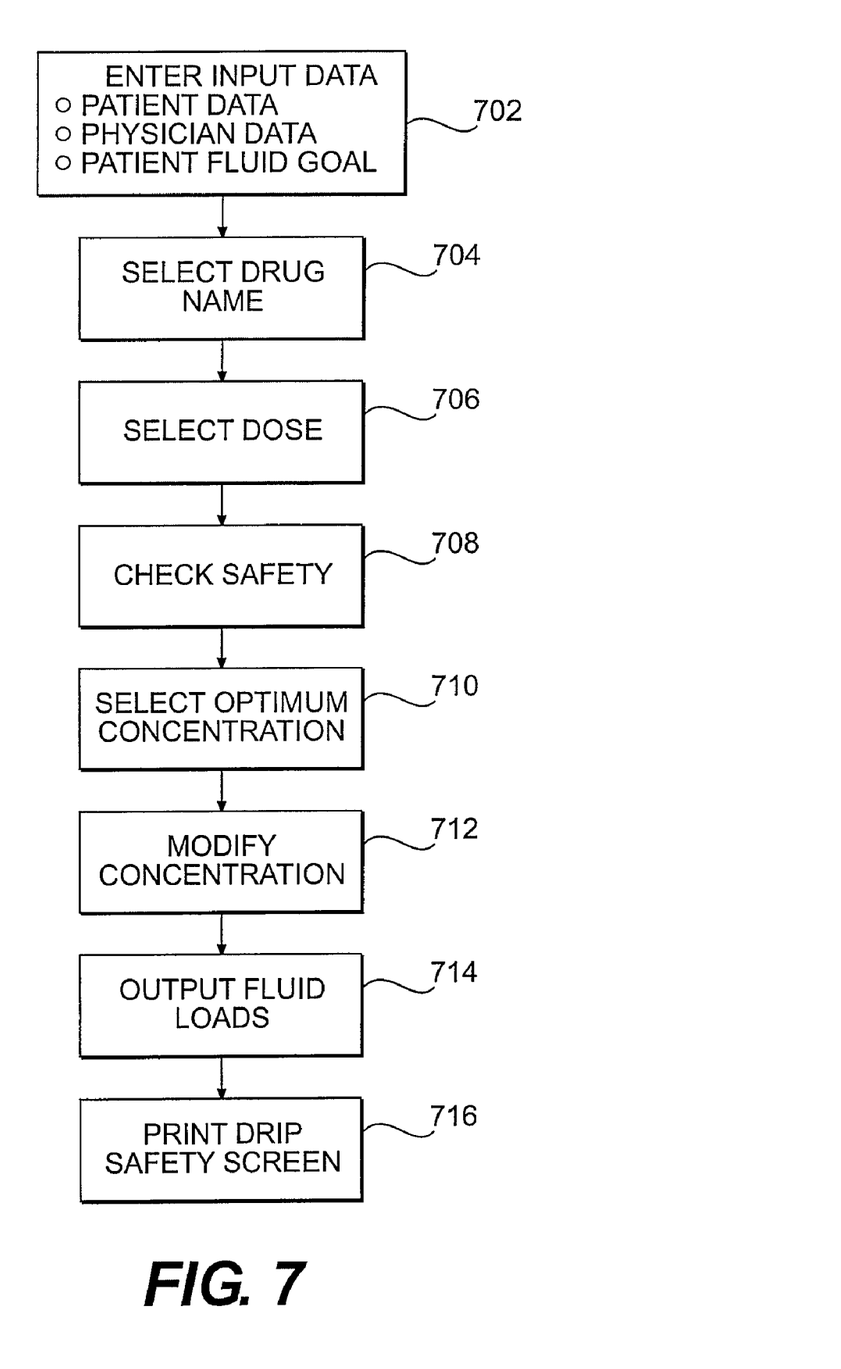
FIG. 7 is a flow chart illustrating an aspect of embodiments of the present invention for assisting physician order entry.

FIG. 7 is a flow chart illustrating an aspect of embodiments of the present invention for assisting physician order entry. In step 702 a user, for example a health care provider, such as a physician and/or a nurse, enters patient data. The patient data can include demographic data such as name, MR number and patient weight. In addition to the patient data, ordering physician data is entered. The ordering physician data can include data such as ordering physician name and pager number. In addition, patient fluid goal is selected. The patient fluid goal can be in units of mL/kg/day or "times maintenance".

In step 704, the user selects a medication. For example, the medication or drug can be selected by name. According to one embodiment of the present invention, upon selecting the medication, a drug information help box is displayed to the user. The drug information help box displays additional drug information to assist the user in correct drug usage. Such information can include safety alerts, drug usage guidelines, alerts and warnings.

In step 706, the user selects drug dose. To assist the user in selecting an appropriate dosage, embodiments of the present invention display the usual dosage range to the user. In step 708, a safety check is performed. For example, as a safety measure against overdose, embodiments of the present invention display a warning to the user if the user selects a dose greater than the usual range. Embodiments of the present invention further require the user to obtain a second physician signature to confirm unusually high doses. Further, as a safety measure against excessive dosage, embodiments of the present invention, in addition to displaying an alert, prevent ordering of doses greater than 2 times the upper limit of the usual dosage range.

After an appropriate dose is selected, in step 710, the optimum concentration for the medical infusion is determined such that the fluid load resulting from the selected concentration is always within the acceptable fluid load selected by the user. The optimum concentration is determined as described above.

In step 712, the optimum concentrations determined in step 710 can be modified manually by the user if desired. For example, the user may modify the optimum concentrations determined in step 710 to accommodate varying clinical needs of each patient. In addition to modifying the optimum concentration, if desired, the user can add special comments (e.g., nursing instructions) for each drug.

In step 714, the drip rate in mL/hour and fluid load in percentage total fluid limit expressed as times maintenance or ml/kg/day or ml/day for each drip is displayed to the user. In addition, the total drip rate in mL/hour and fluid load in percentage of total fluid limit expressed as times maintenance or ml/kg/day or ml/day is displayed for all drugs.

After drugs and doses are selected, a user can print out the orders for each drug. Prior to printing out the order, however, in step 716, embodiments of the present invention provide a confirmation display to the user. The confirmation screen requires the user to verify input parameters as a safety measure prior to printing out the order. The input parameters requiring confirmation can be any of the input parameters to provide the required level of safety, including for example, patient identity, patient weight, names of drugs selected and doses for each drug.

After drugs and doses are selected, the user prints the final order that is sent to the pharmacy and included in the patient's chart. FIG. 6 illustrates an exemplary order sheet 600 according to an embodiment of the present invention. As shown in FIG. 6, exemplary order sheet 600 includes a basic order section 602. Basic order section 602 includes the name of the drug or medication, the dose, the concentration and the infusion rate, e.g., in mL/hr.

Exemplary order sheet also include a pharmacy compounding instructions section 604. Compounding instructions section 604 comprises a unique pharmacy mnemonic for each drug order generated on the printout as well as the volume of drug to be compounded. For example, the mnemonic for Dopamine, 250 ml infusion volumes is "DOPA2." Entering the unique mnemonic in the pharmacy computer system brings up the correct compounding instructions for the pharmacist. Compounding instructions section 604 also includes the total amount of medication required in terms of total volume. Compounding instructions section 604 also alerts the pharmacy to the availability of commercially available premixed drug concentrations. When such premixed concentrations are available, the pharmacy can use them, thereby eliminating the need for the pharmacy to compound such orders. Compounding instructions section 604 further includes the final concentration, e.g., in mcg/mL.

Exemplary order sheet 600 further includes a nursing instructions section 606. Nursing instructions 606 provides instructions on how to program the infusion pump to correctly infuse the drug at the desired dosage. Embodiments of the present invention use a standard mathematical formula (which varies depending upon the drug used) to double check and confirm drug dosage calculations.

Exemplary order sheet 600 further includes a dose change instructions section 608. In dose change instructions section 608, any dose change orders are entered by physicians.

Exemplary order sheet 600 further includes a drip table 610. Drip table 610 is a dosing table that displays a grid of the entire range of doses and the corresponding infusing rate in mL/hr. Drip table 610 provides an easy reference to ensure the correct infusing rate for any dose range.

Embodiments of the present invention also incorporate safety features, some of which have been described above. For example, embodiments of the present invention can incorporate one or more of the following safety features:

(1) All fields must be entered—A user cannot proceed if any field is incomplete. This requirement ensures that critical safety data such as patient weight, patient identification and name of the ordering physician are not inadvertently omitted.

(2) Drug reference information is displayed whenever a drug is selected. This feature provides useful information and safety alerts to the ordering physician at the point of ordering.

(3) Safety against excessive dosage—As described above, embodiments of the present invention can alert the user if the user selects a dose that is greater than the usual range and require the user to confirm the dose by a second physician. If the selected dose is greater than 2 times the upper limit of the usual dose range, embodiments of the present invention can prevent the user from proceeding with the order. A factor other than 2 can be used in embodiments of the present invention. It would be apparent to those skilled in the art that additional safety features could be added if desired.

(4) Drugs using a continuous infusion require multiple calculation steps. Embodiments of the present invention, as described above, perform all required calculations thus eliminating errors often introduced during manual calculations.

(5) All orders are in the form of a computer-generated printout, thereby eliminating errors resulting from illegible handwriting.

(6) The order sheet printout output by embodiments of the present invention provides comprehensive, step-by-step instructions to the pharmacist for compounding each drug infusion and to the nurse for correct infusion of each drug. This feature minimizes errors resulting from incorrect compounding and incorrect infusion of the drug.

(7) The order sheet printout provides a dosing table showing infusion rates at all dose ranges. This feature provides the nurse with a quick reference to ensure that the dose ordered is being infused at the correct infusion rate.

Figure 8:
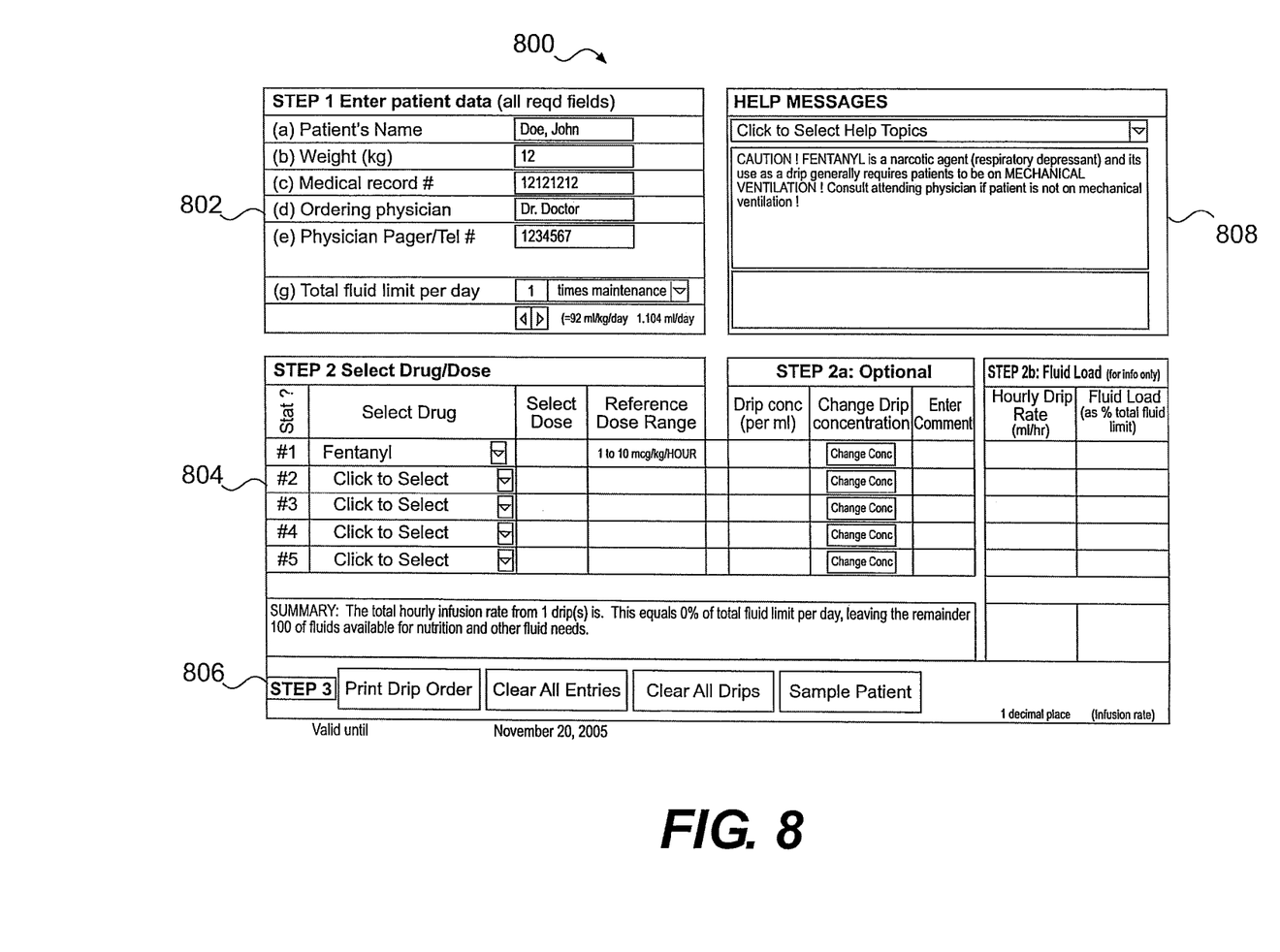
FIG. 8 is an exemplary form that can be displayed to a user for entering a drip order according to an embodiment of the present invention.

FIG. 8 is an exemplary form 800 that can be displayed to a user for entering a drip order according to an embodiment of the present invention. For example, form 800 is an exemplary screen shot that can be displayed on display associated with a computer on which embodiments of the present invention execute.

According to an embodiment of the present invention, form 800 includes a section 802 for entering patient data. The patient data can include data such as patient name, patient weight, total fluid limit per day for the patient, medical record number associated with the patient, name of the ordering physician, and contact information for the ordering physician.

Form 800 further includes a section 804 for selecting the drug to be administered and its dose. Entries in section 804 include drug name and dose as well as desired concentration changes and associated comments. Section 804 also provides a reference dose range to assist the user. Section 804 also displays fluid load based on the user's inputs.

Form 800 also includes an administrative section 806. Administrative section 806 includes options for printing the drip order, clearing all entries, clearing drips and displaying an exemplary drip order.

The present invention also includes drugs made in accordance with any of the methods described herein. Such drugs include, for example, drugs made in accordance with the optimum concentrations determined by the techniques described above and/or using the system described above.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising:
   determining a first infusion rate for administering a first medication to a patient;
   determining a fluid load on the patient based at least in part on the first infusion rate;
   determining whether the fluid load exceeds a predetermined threshold for the patient that represents a total fluid limit; and
   if it is determined that the fluid load exceeds the predetermined threshold, then operating an apparatus to inhibit administering the first medication to the patient at the first infusion rate.

2. A method as recited in claim 1, wherein:
   the method further comprises determining a weight of the patient;
   the predetermined threshold represents the total fluid limit per unit of weight of any patient; and
   determining whether the fluid load exceeds the predetermined threshold further comprises determining whether a ratio of the fluid load divided by the patient weight exceeds the predetermined threshold.

3. A method as recited in claim 1, wherein the the total fluid limit is based on 120 milliliters per day per kilogram of weight of any patient.

4. A method as recited in claim 1, wherein the total fluid limit is fluid maintenance rate times a predetermined percentage that is substantively less than 100%.

5. A method as recited in claim 4, wherein the predetermined percentage is less than about 8%.

6. A method as recited in claim 1, wherein operating the apparatus to inhibit administering the first medication to the patient at the first infusion rate further comprises presenting data that indicates a different concentration for a supply of the first medication than used for determining the first infusion rate.

7. A method as receipted in claim 6, wherein operating the apparatus to inhibit administering the first medication to the patient at the infusion rate further comprises presenting data that indicates a different infusion rate based on the different concentration for the supply of the medication.

8. A method as recited in claim 1, wherein operating the apparatus to inhibit administering the first medication to the patient at the first infusion rate further comprises presenting an alarm that indicates an unsafe infusion rate.

9. A method as recited in claim 1, wherein operating the apparatus to inhibit administering the first medication to the patient at the first infusion rate further comprises presenting data that indicates an unsafe infusion rate.

10. A method as recited in claim 9, wherein data that indicates an unsafe infusion rate is at least one of a color or grayscale or crosshatching associated with the first infusion rate.

11. A method as recited in claim 1, further comprising if it is determined that the fluid load does not exceed the predetermined threshold, then presenting data that indicates one of a low infusion rate or an intermediate infusion rate or a maximum infusion rate.

12. A method as recited in claim 11, wherein data that indicates a low infusion rate or an intermediate infusion rate or a maximum infusion rate is at least one of a color or grayscale or crosshatching associated with the first infusion rate.

13. A method as recited in claim 1, wherein operating the apparatus to inhibit administering the first medication to the patient at the first infusion rate further comprises presenting data that indicates the fluid load.

14. A method as recited in claim 1, wherein:
   the method further comprises determining a second infusion rate for administering a second medication to the patient; and
   determining the fluid load further comprises determining the fluid load based at least in part on the second infusion rate.

15. An apparatus comprising:
   means for determining a first infusion rate for administering a first medication to a patient;
   means for determining a fluid load on the patient based at least in part on the first infusion rate;
   means for determining whether the fluid load exceeds a predetermined threshold for the patient that represents a total fluid limit; and
   means for causing an action to inhibit administering the first medication to the patient at the first infusion rate, if it is determined that the fluid load exceeds the predetermined threshold fluid load.

16. A non-transitory computer-readable external mass storage carrying a computer program, wherein execution of the computer program by a microprocessor causes the microprocessor to, at least:
   determine a first infusion rate for administering a first medication to a patient;
   determine a fluid load on the patient based at least in part on the first infusion rate;
   determine whether the fluid load exceeds a predetermined threshold for the patient that represents a total fluid limit and cause an action to inhibit administering the first medication to the patient at the first infusion rate, if it is determined that the fluid load exceeds the predetermined threshold fluid load.

17. An apparatus comprising:
    one or more microprocessors;
    a display;
    a computer-readable internal memory or external mass storage; and
    a computer program stored on the computer-readable memory or external mass storage, wherein execution of the computer program by the one or more microprocessors causes the one or more microprocessors to determine a first infusion rate for administering a first medication to a patient;
    determine a fluid load on the patient based at least in part on the first infusion rate;
    determine whether the fluid load exceeds a predetermined threshold for the patient that represents a total fluid limit; and
    cause an action to inhibit administering the first medication to the patient at the first infusion rate, if it is determined that the fluid load exceeds the predetermined threshold fluid load.

* * * * *